United States Patent
Chao et al.

(10) Patent No.: US 7,226,453 B2
(45) Date of Patent: Jun. 5, 2007

(54) INSTRUMENT FOR INSERTING, ADJUSTING AND REMOVING PEDICLE SCREWS AND OTHER ORTHOPEDIC IMPLANTS

(75) Inventors: Nam T. Chao, Marlborough, MA (US); Chris Rybicki, Stamford, CT (US); Dale Whipple, East Taunton, MA (US)

(73) Assignee: Depuy Spine, Inc., Raynham, MA (US)

( * ) Notice: Subject to any disclaimer, the term of this patent is extended or adjusted under 35 U.S.C. 154(b) by 133 days.

(21) Appl. No.: 10/815,888

(22) Filed: Mar. 31, 2004

(65) Prior Publication Data

US 2005/0228400 A1 Oct. 13, 2005

(51) Int. Cl.
*A61B 17/58* (2006.01)
(52) U.S. Cl. .......................... 606/104; 606/99
(58) Field of Classification Search ................ 606/104, 606/99
See application file for complete search history.

(56) References Cited

U.S. PATENT DOCUMENTS

| | | | | |
|---|---|---|---|---|
| 1,410,088 A * | 3/1922 | White | ................... | 81/448 |
| 2,248,054 A * | 7/1941 | Becker | ................... | 81/457 |
| 2,593,622 A * | 4/1952 | Stanelle | ................... | 81/448 |
| 3,604,487 A * | 9/1971 | Gilbert | ................... | 81/443 |
| 5,139,499 A | 8/1992 | Small et al. | | |
| 5,484,440 A * | 1/1996 | Allard | ................... | 606/73 |
| 5,667,513 A * | 9/1997 | Torrie et al. | ................... | 606/104 |
| 5,720,751 A * | 2/1998 | Jackson | ................... | 606/86 |
| 6,139,549 A * | 10/2000 | Keller | ................... | 606/61 |
| 6,183,472 B1 * | 2/2001 | Lutz | ................... | 606/61 |
| 6,660,006 B2 * | 12/2003 | Markworth et al. | ................... | 606/61 |
| 2002/0198534 A1 | 12/2002 | White et al. | | |
| 2004/0068269 A1 * | 4/2004 | Bonati et al. | ................... | 606/104 |
| 2004/0147937 A1 * | 7/2004 | Dunbar et al. | ................... | 606/99 |
| 2005/0149053 A1 * | 7/2005 | Varieur et al. | ................... | 606/104 |
| 2005/0165408 A1 * | 7/2005 | Puno et al. | ................... | 606/99 |

* cited by examiner

*Primary Examiner*—Paul B. Prebilic
(74) *Attorney, Agent, or Firm*—Lahive & Cockfield, LLP

(57) ABSTRACT

An instrument for inserting, adjusting and engaging an implant, such as a polyaxial screw of a spinal fixation system, includes at least one retratractable tab for engaging a corresponding recess on the implant and a shaft that moves relative to the retractable tab. The movable shaft selectively moves the tab between an expanded position for engaging the recess and a retracted position out of engagement with the recess. The shaft selectively engages a portion of the implant to rigidify the implant after the retractable tab engages the recess. The axially extending shaft may be disposed within an axially extending passageway of a body assembly. A rotatable collar surrounding the body assembly is coupled to the shaft for moving the shaft relative to the retractable tab.

4 Claims, 9 Drawing Sheets

SECTION A-A

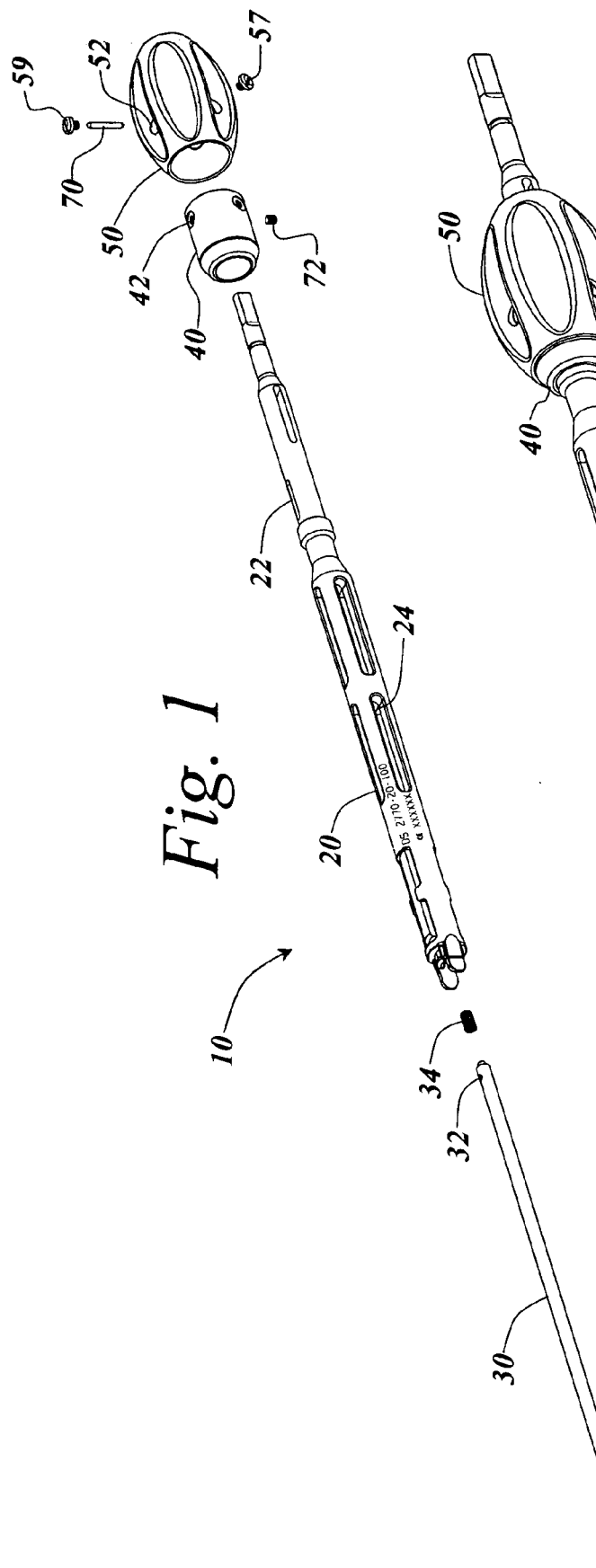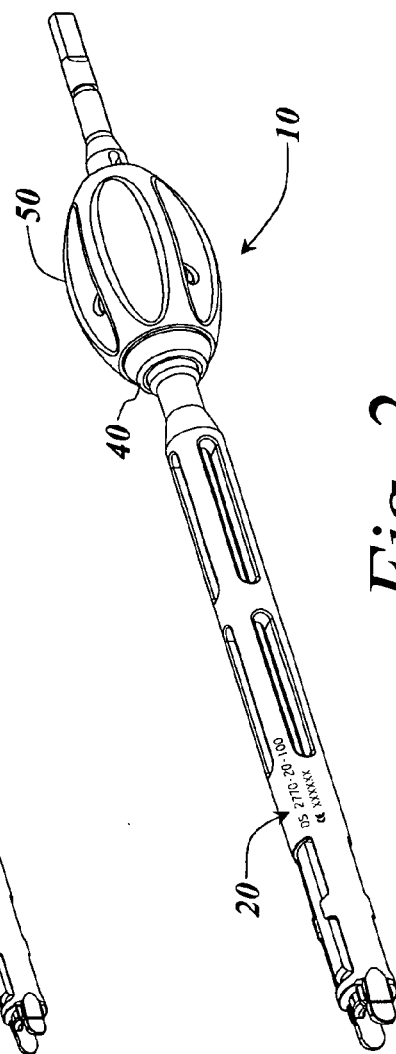

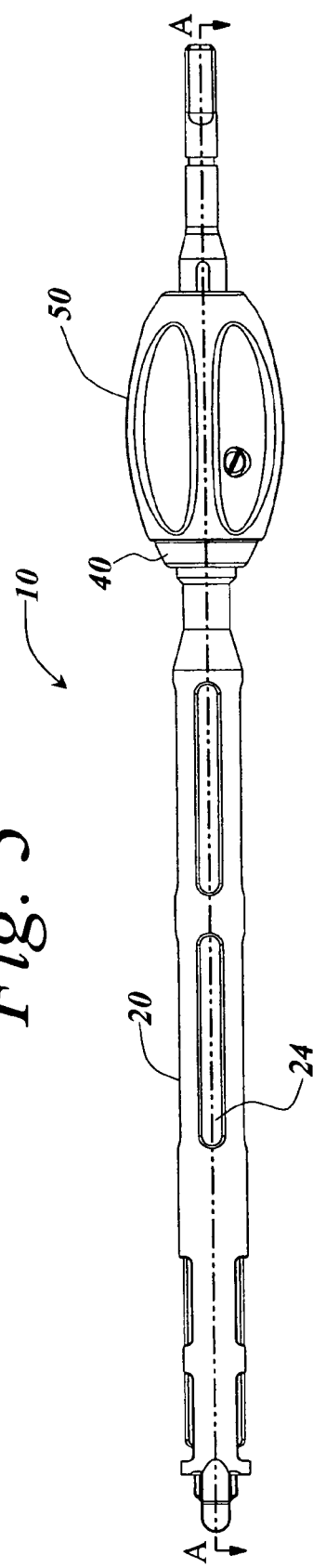
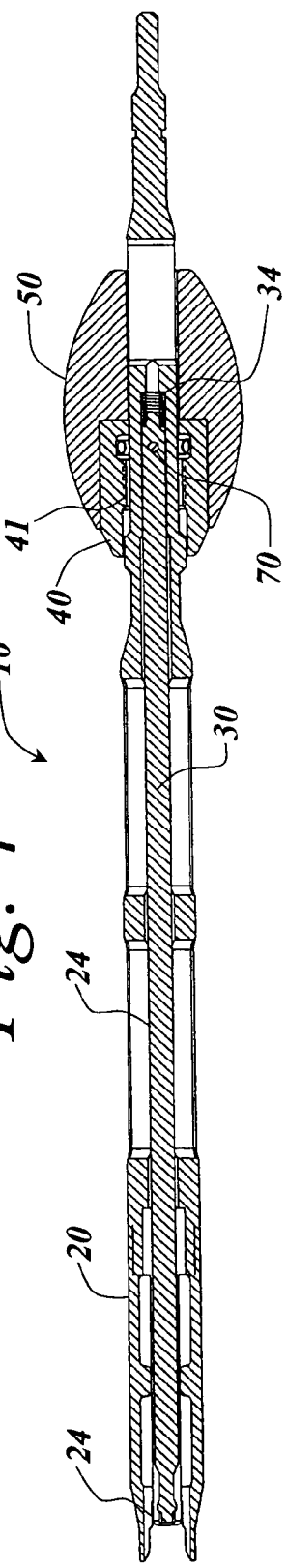
Fig. 3
Fig. 4 SECTION A-A

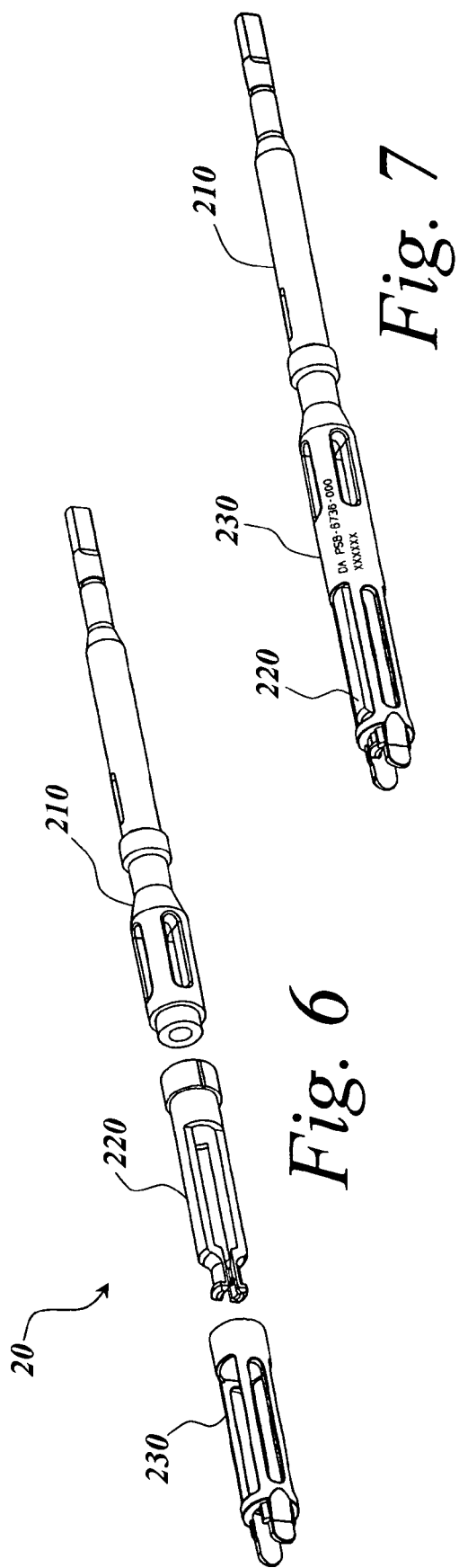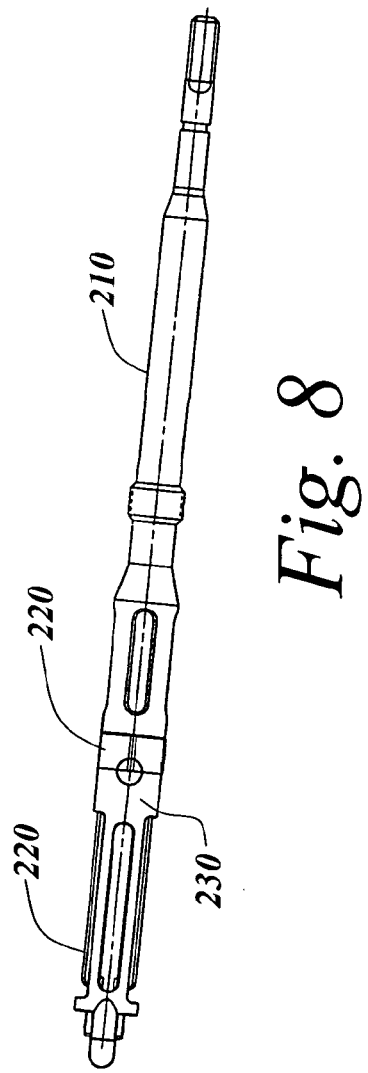

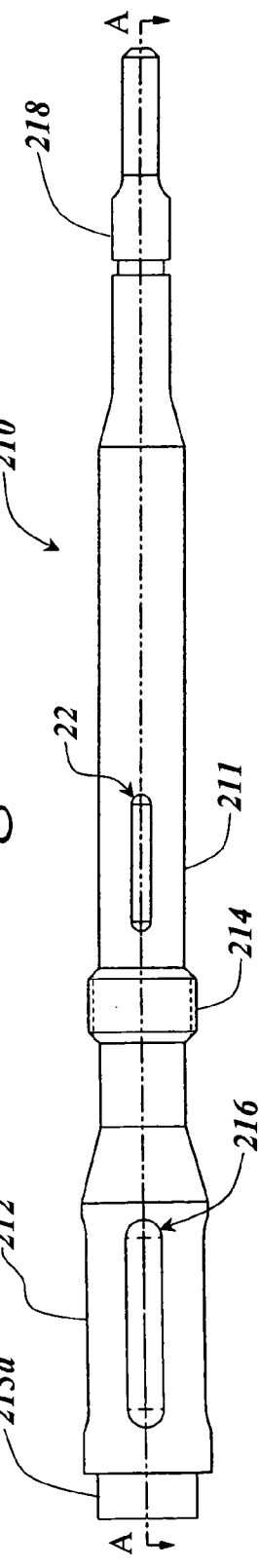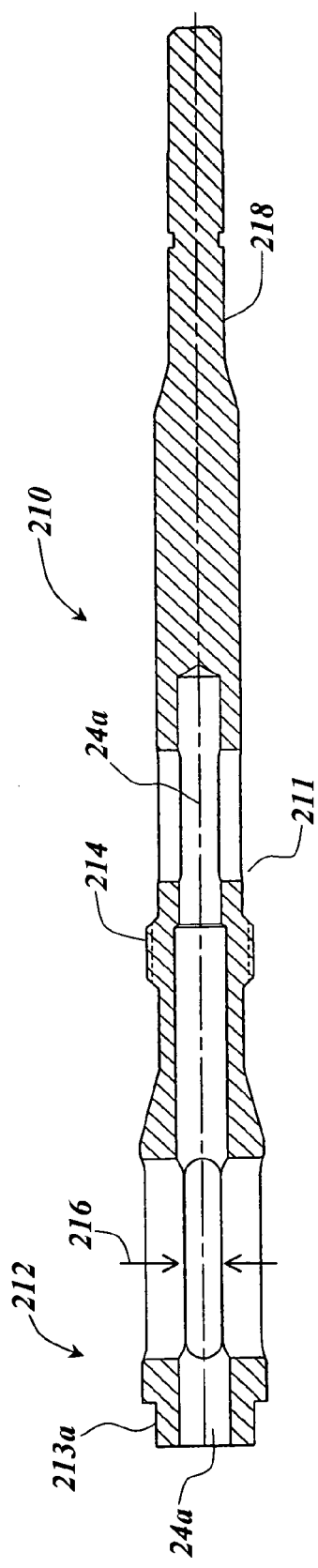

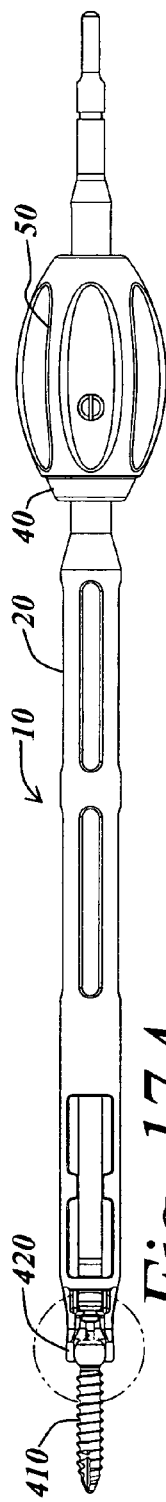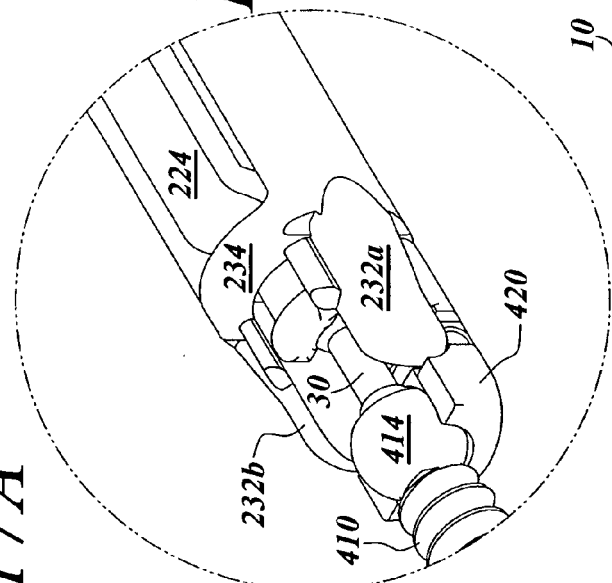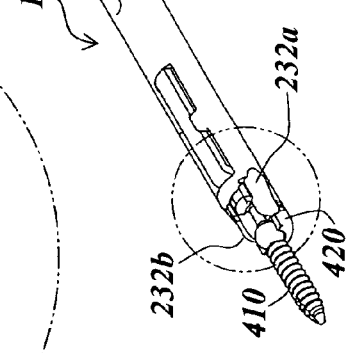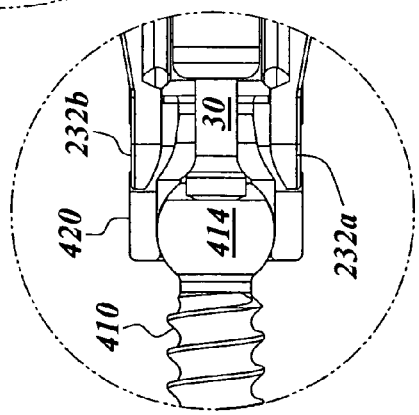
Fig. 17A
Fig. 17B
Fig. 17C
Fig. 17D

INSTRUMENT FOR INSERTING, ADJUSTING AND REMOVING PEDICLE SCREWS AND OTHER ORTHOPEDIC IMPLANTS

FIELD OF THE INVENTION

The present invention relates to spinal fixation devices used in orthopedic surgery. More particularly, the present invention relates to an instrument for inserting, adjusting and removing a spinal implant, such as a polyaxial pedicle screw.

BACKGROUND OF THE INVENTION

Spinal fixation systems may be used in orthopedic surgery to align, stabilize and/or fix a desired relationship between adjacent vertebral bodies. Such systems typically include a spinal fixation element, such as a relatively rigid fixation rod or plate, that is coupled to adjacent vertebrae by attaching the element to various anchoring devices, such as hooks, bolts, wires or screws. The spinal fixation element can have a predetermined contour that has been designed according to the properties of the target implantation site and, once installed, the spinal fixation element holds the vertebrae in a desired spatial relationship, either until desired healing or spinal fusion has occurred, or for some longer period of time.

Spinal fixation elements can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a spinal fixation element receiving element, which, in spinal rod applications, is usually in the form of a U-shaped slit formed in the head for receiving the rod. In many pedicle screws, the head is movable and preferably pivotable in all directions, relative to the shaft. The ability to move the head relative to the anchoring portion of the screw facilitates alignment and seating of a rod connecting a plurality of screws A set-screw, plug, cap or similar type of closure mechanism is used to lock the rod into the rod-receiving portion of the pedicle screw. In use, the shank portion of each screw is then threaded into a vertebra, and once properly positioned, a fixation rod is seated through the rod-receiving portion of each screw and the rod is locked in place by tightening a cap or similar type of closure mechanism to securely interconnect each screw and the fixation rod. Other anchoring devices include hooks and other types of bone screws Polyaxial screws and other implants having movable components are often difficult to handle. To insert and remove the screw, the components of the implant must be made rigid relative to each other, to enable rotation of the shaft in a desired direction by engaging the head. Current drivers for inserting polyaxial screws are incapable of also unscrewing the polyaxial screw. For example, while conventional polyaxial screw drivers are able to maintain the screw rigid while rotating the shaft in a direction for insertion, the rotation in the reverse direction fails to maintain a rigid screw, causing the head to rotate around the shaft without rotating the shaft.

SUMMARY OF THE INVENTION

The present invention provides an instrument for inserting, adjusting and removing an implant in a spinal fixation system, such as a polyaxial pedicle screw. The instrument includes a body assembly for mating with a first portion of the implant and an inner shaft disposed within a passage of the body assembly for engaging a second portion of the implant. The inner shaft moves within the passage to selectively fix the position of the second portion relative to the first portion and to selectively secure the body assembly to the first portion of the implant. A threaded collar selectively extends and retracts the inner shaft relative to the body assembly and secures the position of the inner shaft relative to the body assembly.

According to a first aspect, an instrument for engaging an implant is provided. The instrument comprises an engagement mechanism for selectively engaging a first portion of the implant and a shaft movable relative to the engagement mechanism for selectively engaging a second portion of the implant to rigidify the implant. The shaft also actuates the engagement mechanism to engage with the first portion.

According to another aspect, a screwdriver for a polyaxial screw comprises a body assembly, an inner shaft, a threaded rotatable collar and a coupling pin. The body assembly defines an axially extending inner passageway. The body assembly includes a plurality of retractable tabs for selectively engaging recesses on the polyaxial screw and a tip defining a plurality of alignment protrusions for mating with a rod-receiving opening on the polyaxial screw to align the screwdriver with the polyaxial screw. The inner shaft applies distraction between a head of the polyaxial screw and a shaft of the polyaxial screw to rigidify the screw. The inner shaft is movably disposed within the passageway. The threaded rotatable collar surrounds the body assembly and has a threaded inner surface. The coupling pin extends from the inner shaft and interfering with the threaded inner surface of the collar to couple the inner shaft to the threaded collar.

According to another aspect of the invention, a method of engaging a polyaxial screw comprises the steps of moving a shaft relative to an engagement mechanism of an instrument to actuate the engagement mechanism to engage a first portion of the polyaxial screw and moving the shaft in a second direction relative to the engagement mechanism to rigidify the polyaxial screw.

According to still another aspect, a screwdriver for a polyaxial screw comprises retractable tabs formed on a distal end of the screwdriver for selectively engaging recesses on the head portion of the polyaxial screw, and a shaft movable relative to the retractable tabs. The shaft selectively engages a shaft portion of the polyaxial screw to fix the shaft portion relative to the head portion and actuates the retractable tabs to engage with the recesses.

BRIEF DESCRIPTION OF THE FIGURES

FIG. 1 is an exploded view of an instrument for engaging an orthopedic implant according to an embodiment of the invention.

FIG. 2 is a perspective view of the assembled instrument of FIG. 1.

FIG. 3 is a side view of the assembled instrument of FIG. 1

FIG. 4 is a cross-sectional view of the instrument along section A—A of FIG. 3.

FIG. 6 is an exploded view of the body assembly of the instrument of FIG. 1.

FIG. 7 is an assembled perspective view of the body assembly of FIG. 6.

FIG. 8 is a side view of the body assembly of FIG. 6.

FIG. 9 is a cross-sectional side view of the drive shaft of the body assembly of FIG. 6.

FIG. 10 is a side view of the drive shaft of the body assembly of FIG. 6.

FIGS. 17A–17D illustrate the instrument of FIGS. 1–4 after engaging and rigidifying the implant of FIG. 5.

DETAILED DESCRIPTION OF THE INVENTION

Figure 5:
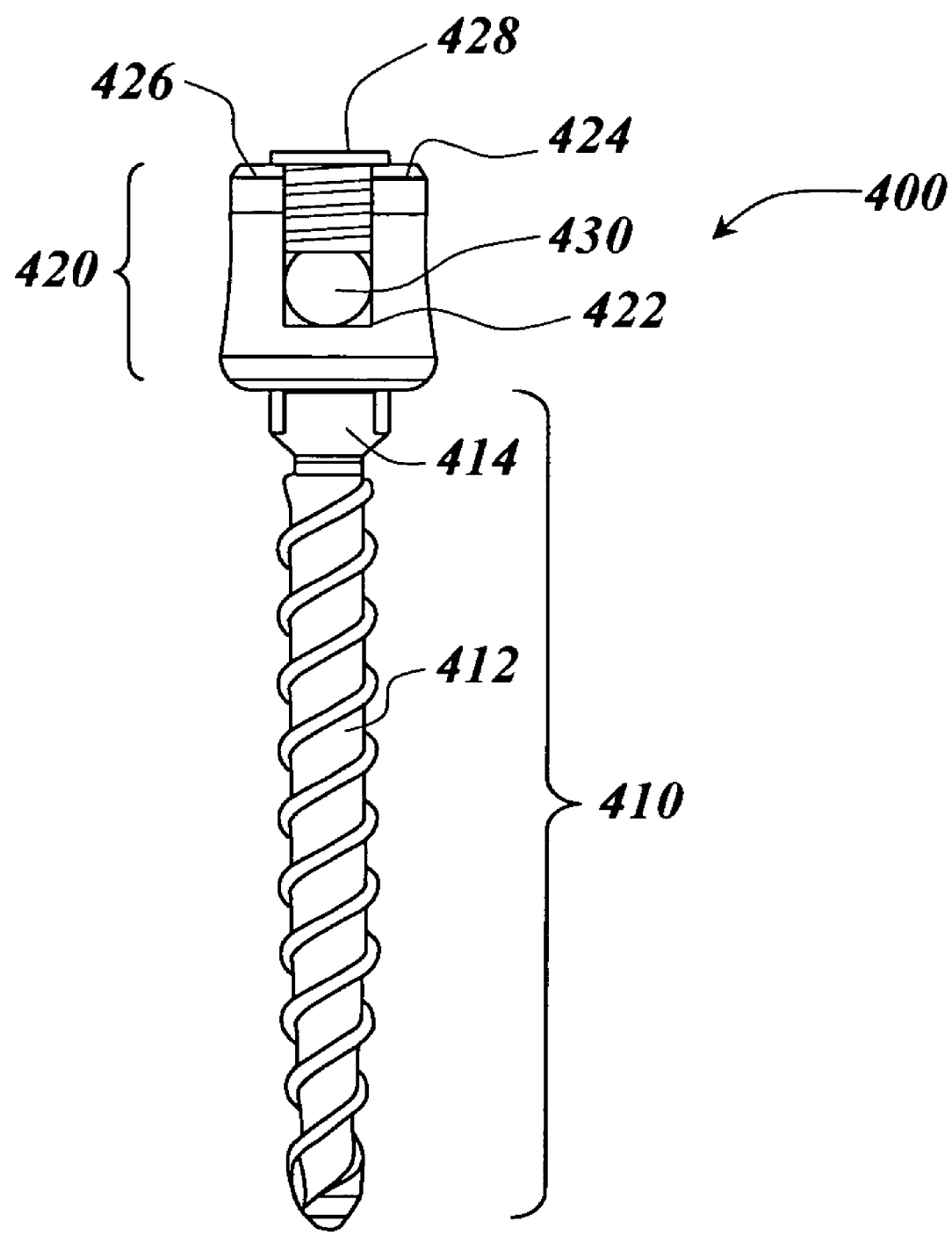
FIG. 5 illustrates a polyaxial screw suitable for use with the instrument of FIG. 1.

The present invention provides an improved instrument for engaging an implant, such as a polyaxial screw, in a spinal fixation system. The instrument can be used to straighten, insert, adjust and/or remove an implant without modification or replacement of the instrument. The present invention will be described below relative to an illustrative embodiment. Those skilled in the art will appreciate that the present invention may be implemented in a number of different applications and embodiments and is not specifically limited in its application to the particular embodiments depicted herein.

FIG. 1 illustrates an exploded view of an instrument 10 for engaging an orthopedic implant, such as a polyaxial screw used in a spinal fixation system, according to an illustrative embodiment of the invention. The instrument 10 can be used with any suitable orthopedic implant, such as monoaxial screw assemblies and hooks and is not limited to use with polyaxial screws per se. FIGS. 2 and 3 are perspective and side views, respectively, of the assembled instrument 10, while FIG. 4 is a cross-sectional side view of the assembled instrument. The instrument 10 includes a body assembly 20 for engaging a first portion of the orthopedic implant, for example, the head of a polyaxial screw. The instrument 10 further includes an inner shaft 30 for engaging a second portion of the orthopedic implant, for example, the shaft of a polyaxial screw. The inner shaft 30 fixes the position of the second portion relative to the first portion and makes the implant rigid. The inner shaft 30 is inserted in an axial passageway 24 of the body assembly, which extends along a longitudinal axis A—A of the instrument 10. The inner shaft is positioned within the axial passageway 24 such that a pin-receiving hole 32 on the inner shaft 30 aligns with an axially extending slot 22 on the body assembly 20.

The instrument 10 further includes a threaded collar 40 encircling the body assembly 20 and a handle 50 surrounding the threaded collar 40 when the instrument is assembled. The handle 50 may be sized and shaped to facilitate handling by the user. For example, in the illustrative embodiment, the handle 50 comprises an egg-shaped knob sized and shaped to fit comfortably in an operator's hand and including a plurality of recesses for allowing the user to grip the handle 50, though one skilled in the art will recognize that the handle is not limited to the illustrative configuration.

A locking mechanism, illustrated as a set of screws 59, couples the handle 50 to the collar 40 and secures the position of the collar 40 relative to the handle 50. The threaded collar 40 and handle 50 cooperate to selectively move the inner shaft 30 in axial direction relative to the body assembly 20.

A coupling mechanism, illustrated as a pin 70, movably couples the inner shaft 30 to the handle 50 and threaded collar 40. The pin 70, which is inserted in a pin hole 32 on the inner shaft 30, extends perpendicular to the inner shaft 30 and engages a groove on the threaded inner surface 41 of the threaded collar 40. According to an alternate embodiment, the coupling mechanism may comprise a protrusion extending from the inner shaft 30 configured to interface with the threaded collar 40. In such an embodiment, the threaded collar and/or handle may be split into a plurality of segments to facilitate assembly of the instrument 10. The coupling mechanism is not limited to these embodiments and may comprise any suitable means for coupling the inner shaft to the handle and threaded collar to allow the inner shaft 30 to selectively advance and retract within the passageway 24.

The components of the instrument 10 can be formed of any suitable material or materials known in the art, including, but not limited to surgical stainless steel, titanium, plastic, and mixtures thereof.

The axially extending slot 22 on the body assembly allows the inner shaft to axially move a limited distance within the internal passageway 24. When the pin 70 abuts a front end of the slot 22, closest to the distal tip of the instrument, the inner shaft extends beyond the tip of the body assembly. When the pin 70 abuts the back end of the slot 22, closest to the proximal end of the instrument, the front end of the inner shaft retracts within the body assembly, as described in detail below.

The pin 70 cooperates with the threaded inner surface 41 of the threaded collar 40 to move the inner shaft 30 in an axial direction along the length of the axially extending slot 22 when the collar rotates about the body assembly. The axial shaft 30 can be moved by axially moving the threaded collar relative to the body assembly or by rotating the handle 50 to cause the collar 40 to rotate around the body assembly 20. For example, by rotating the handle 50 and collar 40 in a first direction to tighten the handle and collar relative to the body assembly, the threads on the collar force the pin 70 forward (i.e., toward the tip of the instrument) within the slot, causing the inner shaft 30 to advance axially within the passage 24. When the handle 50 and collar rotate in a reverse direction to loosen the handle, the threads pull the pin back, causing the inner shaft to retract within the passage 24.

As shown, the handle 50 includes a pin hole 52 for inserting the pin 70 through the handle. The collar 40 includes a pin hole 42 for inserting the pin 70 through the collar. To assemble the instrument 10, the pin holes 52, 42 and 32 and the axially extending slot 22 are first aligned and the pin 70 is passed through the handle pin hole 52 and collar pin hole 42, and into the inner shaft pin hole 32. A set screw 72 locks the pin 70 to the inner shaft 30 after the pin is inserted, such that the pin 70 extends from the inner shaft and inserted in a groove on the inner surface of the threaded collar. As shown, a set screw 72 is inserted into the aligned pin holes after the pin to lock the pin 70 in position.

A biasing spring 34 may also be provided for biasing the inner shaft 30 in a first position relative to the body assembly 20.

FIG. 5 illustrates an orthopedic implant, illustrated as a polyaxial screw 400 suitable for use with the instrument of the present invention. One skilled in the art will recognize that the instrument 10 is not limited to use with a polyaxial screw, such as the polyaxial screw shown in FIG. 5, and that the instrument may be used to engage, insert and/or remove any suitable implant, such as a monoaxial screw and/or a hook. The illustrated polyaxial screw 400 includes a threaded shaft portion 410 and a head portion 420 that is movably coupled to the threaded shaft portion. The threaded shaft portion includes shaft 412 for engaging bone, which includes an external thread or other suitable bone engagement mechanism for engaging bone. The threaded shaft portion 410 includes a substantially spherical joint portion 414 for movably mounting the head portion on the shaft portion. The spherical shape of the joint allows the head to pivot in all directions relative to the shaft portion, though the joint portion may alternatively have any suitable shape for connecting the head portion. The joint portion 414 may include a flat top surface including a recess or other feature configured to engage the inner shaft 30 of the instrument 10, as described in detail below.

The head portion 420 has a substantially U-shaped cross-section forming an opening 422 defined by walls 424, 426 for receiving a rod 430 or other component of a spinal fixation system. The inner surface of the walls 424, 426 includes a recess that engages the springed fingers of the body assembly. The walls 424, 426 may also include a threaded section for receiving a fastening screw 428, such as a set screw or other suitable device, for securing the rod within the opening 422.

As shown in FIG. 6, the body assembly 20 of the instrument 10 of the illustrative embodiment of the invention includes a plurality of interacting components, including a driver shaft 210, an attachment mechanism for releasably engaging the implant, illustrated as a flexible finger component 220, and a tip component 230. When the body assembly 20 is assembled, the finger component 220 is inserted in and received by the tip component 230, and mounted on an end of the driver shaft 210, as shown in FIGS. 7 and 8.

FIGS. 9 and 10 illustrate in detail the driver shaft 210 of the body assembly 20. The driver shaft 210 includes a primary shaft portion 211, on which is formed the longitudinally extending slot 22 and an axially forward portion 212 having a larger diameter than the primary shaft portion. Slots 216 may be formed in the axially forward portion 212 for facilitating sterilization of the instrument and decreasing the weight of the instrument, though the driver shaft 210 may also be formed without the slots 216. A collar 214 may be formed on the primary shaft portion forward from the slot 22 for cooperating with the threaded collar 40. The axially forward portion 212 has a front end 213a configured to receive and engage an end of the finger component 220. The driver shaft 210 further includes an axially extending passageway 24a, comprising a portion of the axially extending passageway 24, for receiving an end portion of the inner shaft 30 when the instrument is assembled. A tail end 218 of the driver shaft 210 is sized and configured to engage an end handle or other tool to facilitate rotation of the body assembly.

As shown in FIGS. 6, 9 and 10, the front end 213a of the driver shaft 210 includes an annular protrusion configured to be inserted in a base 226 on the end of the finger component 220, though one skilled in the art will recognize that any suitable means for coupling the body assembly components together may be used.

Figure 11:
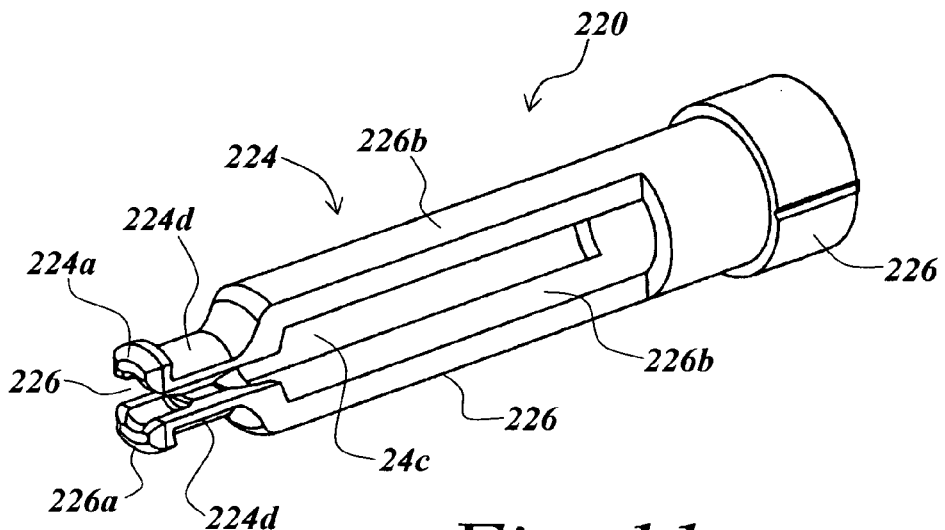
FIG. 11 is a perspective view of the finger portion of the body assembly of FIG. 6.
Figure 12:
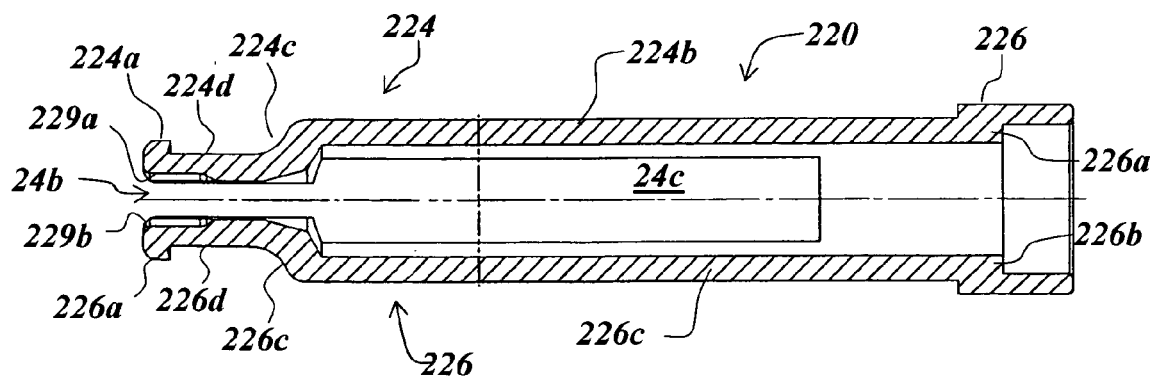
FIG. 12 is a cross-sectional side view of the finger portion of FIG. 11.

The finger component 220, shown in FIGS. 11 and 12, includes a base 226 configured to couple to the end 213a of the axially forward portion and a plurality of flexible finger components 224, 226 for selectively engaging a corresponding portion of the spinal implant. As shown, each of the flexible finger components includes an elongated flexible body 224b, 226b, respectively and retractable tabs 224a, 226a formed on one end that are configured to be inserted in a corresponding recess of the spinal implant to retain the implant on the instrument. As shown, the flexible body and tab of each finger component is connected by an inclined step 224c, 226c, respectively and a neck portion 224d, 226d, respectively, of reduced diameter. The neck portions cooperate to define a front portion 24b of the inner passage 24 extending through the body assembly and the base 226 and finger components define another portion 24c of the passage 24 for receiving the inner shaft. When the components of the body assembly 20 are assembled, as shown in FIGS. 7 and 8, the passage portions 24a, 24b, 24c align to form the axially extending passage 24.

According to an illustrative embodiment of the invention, in a relaxed position, the passage portion 24b defined by the neck portions has a diameter that is smaller than the diameter of the inner shaft 30. When the inner shaft 30 is disposed within the front portion 24b, the shaft 30 pushes against the neck portions to enlarge the passage, pushing the tabs 224a, 224b radially outward. An inner tapering surface 229a, 229b on each neck portion cooperates with the inner shaft, such that when the inner shaft 30 is retracted within the passage, clear of the front portion 24b, the neck portions retract to a relaxed position, compressing and pulling the tabs 224a, 224b radially inward.

According to one embodiment the tabs 224a, 224b on the finger components form a dovetail feature for mating with a corresponding dovetail feature on the implant, though one skilled in the art will recognize that any suitable means for engaging the implant may be used.

The base portion 226 of the finger component has a diameter larger than finger components and includes a radially extending inner step 226a and inner wall 226b for receiving the front end 213a of the driver shaft 210.

One skilled in the art will recognize that the engagement mechanism for selectively engaging the implant and securing the implant to the instrument is not limited to the finger component 220, and that any suitable device for engaging the implant may be used. For example, the engagement mechanism can alternatively engage an outside surface of the implant.

Figure 13:
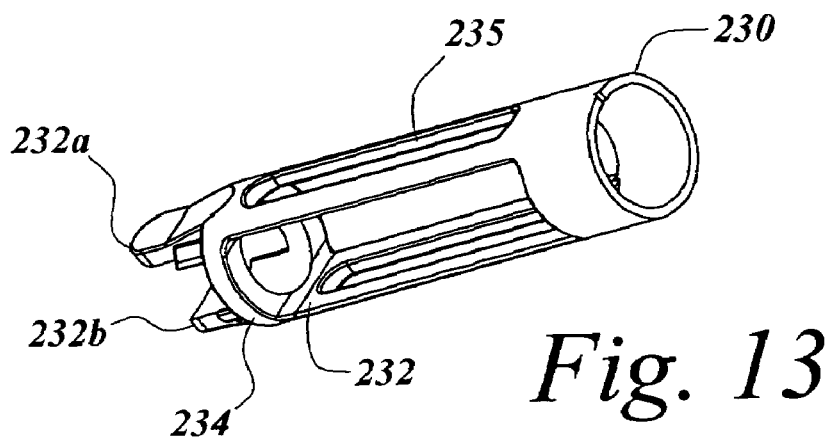
FIG. 13 is a perspective view of the tip portion of the body assembly of FIG. 6.
Figure 14:
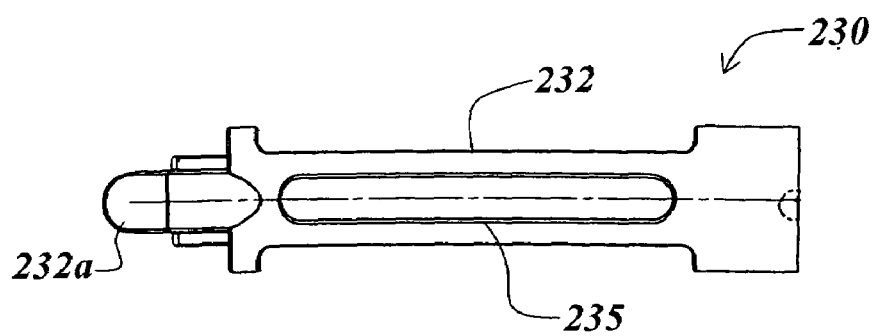
FIG. 14 is a side view of the tip portion of FIG. 13.
Figure 15:
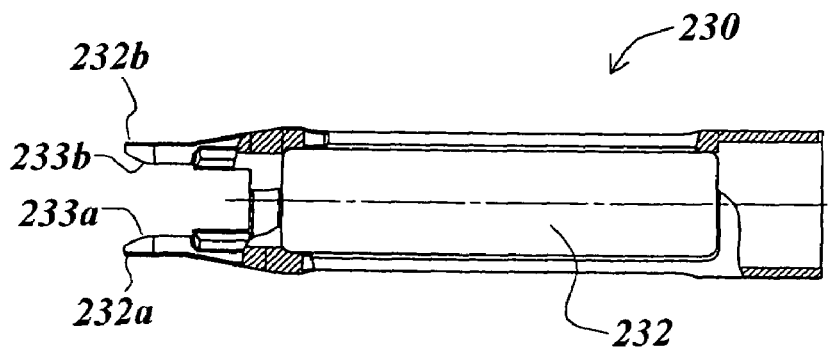
FIG. 15 is a cross-sectional top view of the tip portion of FIG. 13.

The tip portion 230 of the body assembly, shown in FIGS. 13-15, is sized and configured to receive the finger portion 220 therein. As shown, the tip portion 230 includes slots 232 for receiving the body portions of the finger components 224, 226, respectively and a bar 234 configured extend across the step to lock the finger portion in place, such that the tabs extend between the end protrusions. The tip portion 230 may also include side slots 235 for facilitating sterilization of the instrument and decreasing the weight of the instrument, though the tip portion may also be formed without the slots 235.

The tip portion 230 further includes a plurality of end protrusions 232a, 232b for aligning the instrument 10 with the implant. The end protrusions 232a, 232b are configured to mate with one or more openings on the implant to align the implant with the instrument. In the illustrative embodiment, the inner surfaces 233a, 233b of the end protrusions 232a, 232b, respectively, are tapered inward to facilitate alignment of the instrument with the first portion of the implant, such as the head of a polyaxial screw, though one skilled in the art will recognize that the end protrusions may have any suitable configuration.

Figure 16:
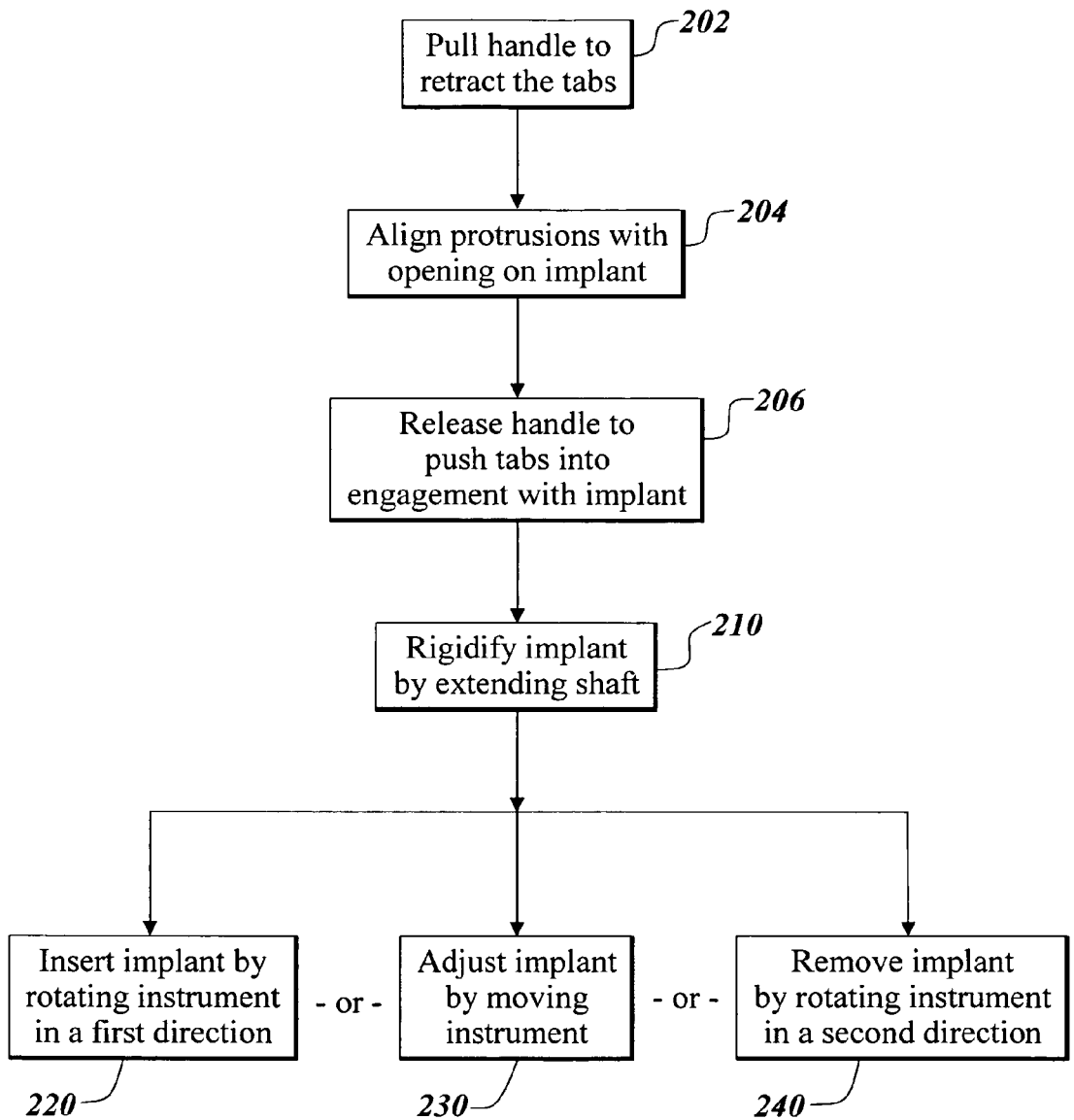
FIG. 16 is a flow chart illustrating the steps involved in inserting a polyaxial screw using the instrument of FIGS. 1–4.

FIG. 16 illustrates the steps involved in using the instrument 10 of the illustrative embodiment of the invention to insert an implant, such as the polyaxial screw 400 shown in FIG. 5. To insert the polyaxial screw using the assembled instrument 10 of the exemplary embodiment of the invention, a user first secures the implant to the instrument in steps 202–206. In the illustrative embodiment, the user secures the implant to the instrument 10 by first pulling the handle 50 against the biasing force of the spring 34 and toward the proximal end (i.e. towards the tail end of the shaft) of the body assembly 10 in step 202. As the handle 50 retracts, the threaded inner surface of the collar 40 pushes the pin 70 toward the proximal end of the slot, which retracts the inner shaft 30 within the passageway 24 and against the biasing force of the spring 34. As the inner shaft 30 retracts within the passage 24, the finger components 224, 226 deflect inwards, causing the tabs 224a, 224b to retract. While the finger components 224, 226 are retracted, the user, in step 204, aligns the end protrusions 232a, 232b on the distal end (i.e., the implant engaging end) of the instrument 10 with an opening of the implant, such as the slot 422 of the screw 400, inserts the end protrusions 232a, 232b in the slot 422, and releases the handle 50 in step 206. After the user releases the handle, the biasing spring 34 pushes the inner shaft 30 forward in the front (distal) portion 24b of the passageway 24. The inner shaft 30 pushes the tabs 224a, 224b outward, causing the tabs to engage corresponding recesses of the implant, for example, internal recesses of a screw head 420, thereby locking the implant to the instrument. As long as the inner shaft 30 is disposed in the front portion 24b of the passageway 24 and pushes the tabs outward, the implant remains locked to the instrument 10 by the cooperation of the tabs of the instrument and the recesses of the implant.

After engaging the implant, the user rigidities the components of the implant in step 210 to enable insertion of the implant, for example by creating a distraction between the shaft portion of a polyaxial screw and a head portion of a polyaxial screw, as shown in FIGS. 17A–17D. According to one aspect, the user first aligns the axis of the shaft portion with the axis of the head portion, for example, by sliding the screw into a holder, such as an alignment guide, or other suitable means. Then, the user distracts the implant using the instrument 10 to create a rigid assembly, in which the shaft portion is fixed relative to the head portion, that can be screwed into bone. In an illustrative embodiment, the user creates a rigid assembly by rotating the handle 50 in a predetermined direction relative to the body assembly 20 to tighten the handle 50 and collar 40 against the body assembly 20. As described above, the rotation of the handle 50 rotates the inner threads of the collar 40, which slides the pin 70 forward within the slot 22 and pushes the inner shaft 30 forward. As the inner shaft 30 extends forward, the inner shaft contacts the joint portion of the implant and creates distraction between the shaft portion and the head portion. In a fully extended position, as shown in FIGS. 17A–17D, the tip of the inner shaft 30 engages a corresponding recess on the joint portion 414, fixing the shaft portion 410 relative to the head portion 420, which is engaged by the tabs 224a, 226a of the instrument.

After the instrument 10 engages and rigidities the implant, such as the polyaxial screw 400, the instrument can be used to screw the implant the bone in step 220 into by rotating the body assembly in an appropriate direction, causing the threaded shaft of the implant to engage and enter the bone.

The same instrument 10 can also be used to adjust an implant already implanted in the bone by engaging and rigidifying the implant, as described above, and then adjusting the implant by rotating or moving the body assembly 20 in step 230.

The instrument 10 can further be used to remove an implant from bone in step 240. To remove an implant, such as a polyaxial screw 400, the instrument first engages a first portion of the implant, for example, the head of a polyaxial screw, by retracting the handle 50 to retract the inner shaft, aligning the tip protrusions with a corresponding opening on the implant and releasing the handle to return the inner shaft to a rest position, causing the tabs to expand and engage corresponding recesses on the implant. Then, the instrument 10 rigidifies the implant by tightening the handle to cause the inner shaft to extend from the rest position and engage a second portion of the implant, for example, the joint portion of a polyaxial screw. After engaging and locking the implant, the instrument 10 can unscrew the implant by rotating the body assembly in a predetermined direction, while maintaining the first and second portions of the implant in a fixed position relative to each other.

The instrument 10 creates a rigid implant assembly that eliminates toggling during insertion and removal, thereby facilitating insertion and removal of an implant, such as a polyaxial screw, during a surgical procedure. Furthermore, the instrument can be used for a plurality of purposes, such as insertion, adjustment and removal of an implant, without requiring modification and/or replacement of any component of the instrument or the instrument as a whole.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense. For example, one skilled in the art will recognize that the instrument of the illustrative embodiment of the invention is not limited to use with polyaxial screws and can be used with any suitable implant for any suitable orthopedic system.

It is also to be understood that the following claims are to cover all generic and specific features of the invention described herein, and all statements of the scope of the invention which, as a matter of language, might be said to fall therebetween.

The invention claimed is:

1. A screwdriver for a polyaxial screw having a head portion movably mounted to a shaft portion, the screwdriver comprising:

a body assembly defining an axially extending inner passageway and including a plurality of retractable tabs for selectively engaging recesses on the polyaxial screw and a tip defining a plurality of alignment protrusions for mating with a rod-receiving opening on the polyaxial screw to align the screwdriver with the polyaxial screw;

an inner shaft for applying distraction between the head portion and the shaft portion to rigidify the screw, the inner shaft being movably disposed within the passageway;

a threaded rotatable collar surrounding the body assembly and having a threaded inner surface; and a coupling pin extending from the inner shaft and interfering with the threaded inner surface of the collar to couple the inner shaft to the threaded collar.

2. The screwdriver of claim 1, further comprising an axially extending slot in the body assembly through which the pin extends.

3. The screwdriver of claim 1, further comprising a handle surrounding and fixed to the rotatable collar.

4. The screwdriver of claim 1, further comprising a spring for biasing the inner shaft to a first position within the inner passageway.

* * * * *